United States Patent [19]

Payton et al.

[11] Patent Number: 4,736,741

[45] Date of Patent: Apr. 12, 1988

[54] NOSEPIECE FOR ADMINISTERING SUPPLEMENTAL OXYGEN

[75] Inventors: Hugh W. Payton, 36 S. Main St., Jeffersonville, Ohio 43128; Harold G. Wyse, Dayton, Ohio

[73] Assignee: Hugh W. Payton, Washington Court House, Ohio

[21] Appl. No.: 244

[22] Filed: Jan. 2, 1987

[51] Int. Cl.⁴ .................. A61M 15/08; A62B 7/00
[52] U.S. Cl. ...................... 128/207.18; 128/206.11; 128/203.22
[58] Field of Search ............ 128/207.18, 203.22, 128/203.23, 206.11, 345; 604/94

[56] References Cited

U.S. PATENT DOCUMENTS 4,273,124  6/1981  Zimmerman ............ 128/207.18
4,660,555  4/1987  Payton .................. 128/207.18

FOREIGN PATENT DOCUMENTS 90190  8/1921  Switzerland ............ 128/345

*Primary Examiner*—William E. Kamm
*Assistant Examiner*—George Manuel
*Attorney, Agent, or Firm*—Biebel, French & Nauman

[57] ABSTRACT

A nosepiece for the administration of supplemental oxygen to a patient through a nasal cavity includes a hollow stem which has one end adapted for the application of oxygen thereto and which has a remote end adapted to be received within a nostril of a patient. A plurality of flexible locating fingers integrally extend from the remote end and are folded back to an outer surface of the stem and are retained in an adjusted position on the stem by an encircling O-ring. The effective width of the nosepiece may be adjusted by sliding the O-ring along the stem to cause the fingers to either lie flatter or bow outwardly from the stem to provide comfort in the retention of the nosepiece within the nasal cavity.

4 Claims, 1 Drawing Sheet

NOSEPIECE FOR ADMINISTERING SUPPLEMENTAL OXYGEN

This application relates to apparatus for administering supplemental oxygen to a patient and, more particularly, to an adjustable nosepiece for unilateral application.

The dual prong nasal cannula is in generally standard use today. It can become quite uncomfortable for a patient. The most commonly used arrangement includes a dual prong nosepiece which is centered in a loop of vinyl tubing. The nosepiece openings are inserted in the nares with the tubing tucked behind the ears. A slide adjustment may be used to draw it tight beneath tne chin. By the third or fourth day of its use, irritation of the skin areas in contact with the cannula has begun. By the fifth day, the majority of patients have begun to use tissues and the like to relieve the soreness under the nose and around the ears. The soreness and irritation is often due to abrasion which is often caused by movement of the tight fitting tube and to the accumulation of moisture between the skin and the vinyl under the nose. In men, growth of the beard can further aggravate the situation.

The comfort of the patient becomes more critical, both to the patient and to the professionals attending the patient when the patient is also fitted with a naso-gastric or Levine tube. Now the nose becomes a fairly cluttered access route, and adhesive tape is often used, by application to the face, to get all the tubes to remain in place.

In cases where supplemental oxygen is required, a patient may suffer from "free floating anxiety" as a result of reduced blood oxygen. Such patient may believe something is wrong but cannot quite identify the problem, and may not be thinking clearly. Often such patients have feelings of claustrophobia and may attempt to remove the cannula despite the fact that doing so may adversely affect the patient's condition. It is not uncommon to find the tubing disconnected and on the floor. Further, patient non-compliance or lack of cooperation may necessitate the use of some more expensive or aggressive means of oxygen adminstration, including face masks or catheters.

Unilateral application offers the possibility of increased comfort over long periods of use, as compared to the two-prong cannula. In the copending application of Payton, Ser. No. 798,519 filed Nov. 18, 1985 now U.S. Pat. No. 4,660,555 issued Apr. 28, 1987, there is described and claimed an improved nosepiece formed of soft elastomeric material in the form of a cone having a skirt with a thin wall section to permit the piece to be inserted into a naris with comfort, and in one embodiment limited adjustment in size (diameter) was provided by a removable skirt portion of the cone. The conical nosepiece did not always retain itself in place, and often depended upon upward support from the oxygen tube.

Experience with a conical nosepiece of the copending application has indicated the desirability of a lighter, more universally adjustable, nares-conforming and self-retaining piece.

SUMMARY OF THE INVENTION

This invention is directed to an adjustable nosepiece for the unilateral application of supplemental oxygen to a patient as delivered through a flexible oxygen tube. The nosepiece of this invention has particular utility when used in combination with the oxygen tube holder of our copending application Ser. No. 932,232 filed Nov. 19, 1986, but it may also be used with other tube-positioning device, as desired, or with none at all.

The improved nosepiece includes a body in the form of a stem or tube through which the oxygen is administered, and further includes an arrangement by which the terminal end of the stem is comfortably retained within a naris. The retaining arrangement includes a plurality of flexible fingers which have proximate ends attached at and surrounding the terminal end of the stem, and with the free or distal ends extending outwardly therefrom. In use, the otherwise free ends are grouped and retained against an outer surface of the stem in an adjustable position, with the intermediate portions free-formed into curved contours. The plurality of fingers together take on a generally pear-shaped configuration, the effective diameter of which can be changed by adjusting the position of the finger ends with respect to the stem. Preferably, the finger ends are retained by a simple O-ring, permitting ease of adjustment, to make wider or narrower the contour of the nosepiece, to conform with comfort to the patient.

An important object of the invention is the provision of an adjustable and comfortable nosepiece for administraton of gas, such as oxygen, to patients.

Another object is the provision of a nosepiece, as outlined above, which may be worn over extended periods with comfort.

A further object of the invention is that of an adjustable nosepeice for unilateral oxygen administration which may be made at low cost.

These and other objects and advantages of the invention will be apparent from the following description, the accompanying drawings, and the appended claims.

DESCRIPTION OF THE PREFERRED EMBODIMENT

Figure 1:
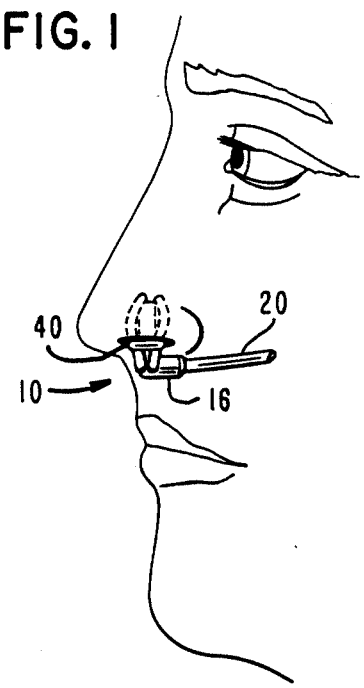
FIG. 1 is a side elevation of a patient using the nosepiece of this invention.

Referring to the figures of the drawing which illustrate a preferred embodiment of the invention, a molded nosepiece made according to the invention is shown at 10 in FIG. 1. The nosepiece 10 may be injection molded essentially as a unitary object from medical grade vinyl, and includes a body having a generally straight portion or stem 15 adapted to be received substantially in one of a patient's nares, with a lower generally right-angled inlet portion 16 which will extend outwardly of the nasal cavity, to receive an oxygen tube 20, as shown in FIG. 1. Each of the body portions 15 and 16 are tubular and hollow to provide an internal pasageway defining an oxygen inlet 21 in the inlet portion 16, and an oxygen outlet 24 at the terminal end 25 of the stem 15. The inlet 21 preferably has a size so as to permit the insertion therein of an end of an oygen-delivery tube 20. Larger tubes may have their ends received over the outer surface of the portion 16, as desired.

Figure 2:
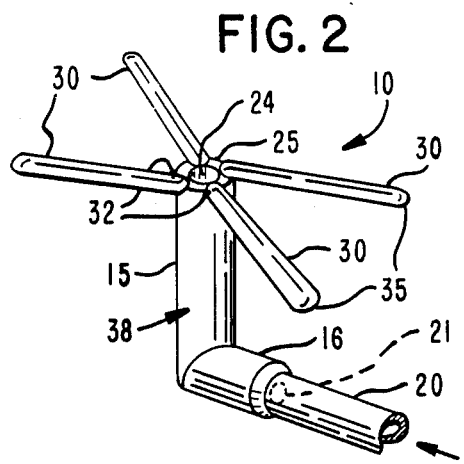
FIG. 2 is a perspective view of the nosepiece after molding.
Figure 3:
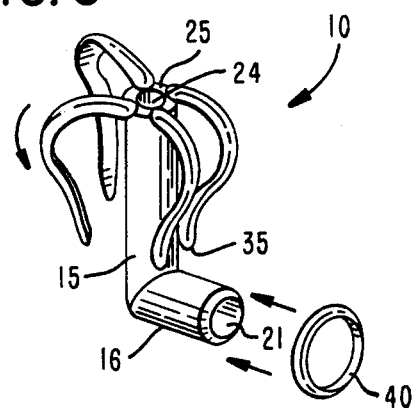
FIG. 3 shows the piece of FIG. 2 with the fingers being folded about the stem to be retained by the O-ring.

Adjustable means for locating the piece comfortably in the nasal cavity include a plurality of generally radially extending fingers 30 formed integrally with the body 15. The fingers have inner or proximate ends 32 attached to the stem 15 at the terminal end 25 in surrounding and non-interferring relation to the outlet 24. While four fingers 30 are preferred, as shown, they may be as few as three, or as many as six or more, but greater numbers of fingers are unwieldly and unnecessary. Four fingers 30 provide a higher degrees of stability than would only three. The remote or distal ends 35 of the fingers, after molding, extend generally radially of the stem, as shown in FIGS. 2 and 5. The ends 35 are normally retained against the outer cylindrical surface 38 of the stem 15 by an encircling and capturing O-ring 40. The O-ring 40 is assembled, after molding, by sliding over the inlet portion 16, as shown in FIG. 3 and onto the stem 15. The ends 35 are captured under the O-ring 40, as shown in FIG. 4.

Figure 4:
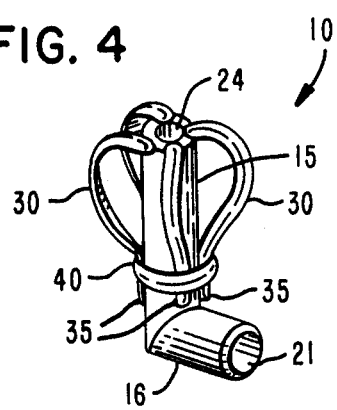
FIG. 4 is a perspective view of the nosepiece ready for use.
Figure 5:
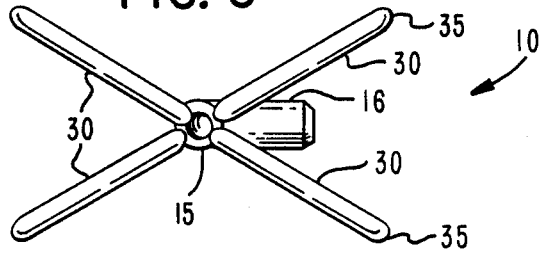
FIG. 5 is a plan view of the nosepiece of FIG. 2 before the fingers are folded.

With reference to FIGS. 3 and 4, it will be seen that the terminal end 25 on the stem 15 is intentionally recessed inwardly or beneath the upper portions of the fingers 30, at the point at which the four fingers join the stem. This avoids a tip on the nasal insert which could unintentionally ride against the nasal septum, creating pain and potential ulceration. The fingers 30, at their upper ends, provide rounded edges so as to void any innernasal irritation.

As shown in FIGS. 3 and 4, the individual fingers 30 have lengths which somewhat exceed that of the stem 15. Also, since the fingers 30 are integrally attached to the stem, at the end 25, the bodies of the fingers bend or curve first outwardly then inwardly in extending between the end 25 and the outer surface 38 under the ring 40, and taken together, assume a pear-shaped configuration. The effective width occupied by the fingers in the nasal cavity may thus be readily varied by adjusting the positions of the finger ends 35 along the stem 15, as by adjusting the position of the O-ring 40.

Figure 6:
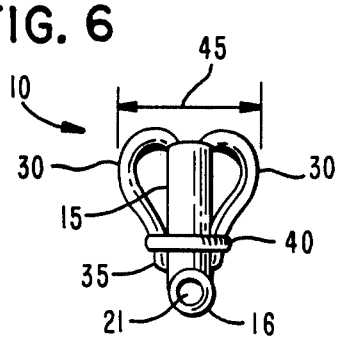
FIG. 6 is a side elevational view of the completed nosepiece, showing the adjustment of the fingers with relation to the stem to occupy a wide space in the nares.
Figure 7:
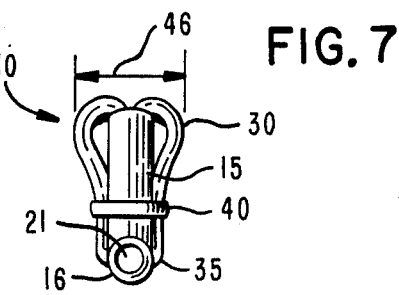
FIG. 7 is a view similar to FIG. 6 but showing the fingers adjusted to occupy a narrow space in the nares.

FIGS. 6 and 7 illustrate the approximate shapes which are assumed by the fingers 30 in the wide or "fat" position 6 and the narrow or "skinny" position of FIG. 7. For example, the wide position, such as for an adult male, assumes a width 45 of about 2.0 cm and the narrow position, a width 46 of about 1.0 cm. The piece 10 may thus be readily adjusted prior to and at use to optimize patient comfort, while assuring retention of the piece within the nasal cavity. Also, it should be noted that the nosepiece of this invention does not occlude the breathing passageway, but permits air to be inhaled or expelled through the spaces between the fingers 30, to alleviate feelings of claustrophobia or discomfort when the air passageway is fully occluded. The nosepiece is preferably formed of a relatively soft grade of medical grade thermoplastic, such as vinyl, with a hardness in the range of 45-100 Shore A. The ring 40 may be formed of the same material.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. An adjustable nosepiece for the administration of supplemental oxygen to a patient comprising:
   means defining a hollow elongated stem having a terminal end,
   means on one end of said stem adapted for attachment of a supply of oxygen,
   means on the said terminal end of said stem defining a plurality of flexible elongated retaining fingers, said retaining fingers each having a proximate end integrally attached to said stem at said terminal end and radiating generally radially therefrom and each having a remote end, each of said fingers being bendable in an arc extending from said attached proximate end with the remote end positioned against said stem, and
   an O-ring surrounding said stem and said remote ends, retaining said remote finger ends against said stem with said fingers formed in a generally pear-shape configuration about said stem, and providing for adjustment of the position of said ends thereon to adjust the extent of spacing of said fingers from said stem.

2. A nosepiece for the administration of supplemental oxygen or the like to the nasal cavity of a patient and adapted to be inserted substantially into said cavity, and being adjustable in size to be self-holding with comfort, comprising:
   a hollow vinyl stem having one end for the application of oxygen thereto and having a remote terminal end adapted to be inserted into a nostril,
   a plurality of flexible, vinyl locating fingers having proximate ends integral to said stem on said terminal end and extending generally radially therefrom,
   each of said finger remote ends being positionable against an outer surface of said stem with said fingers curving from said stem terminal end outwardly then inwardly to said stem forming a generally pear-shaped outine, so that said fingers may be comfortably received within the nasal cavity, and
   means securing said finger ends along the longitudinal axis of said stem to vary the shape of curvature of said fingers with respect to said stem, to change the effective size of said nosepiece.

3. Then nosepiece of claim 2 in which said fingers are of substantially equal length and are four in number.

4. The nosepiece of claim 2 in which said finger remote ends are retained on said stem by an O-ring surrounding said fingers and stem, and slidable axially of said stem to make said change in size.

* * * * *